(12) United States Patent
Chervet et al.

(10) Patent No.: US 6,858,435 B2
(45) Date of Patent: Feb. 22, 2005

(54) METHOD AND SYSTEM FOR PEAK PARKING IN LIQUID CHROMATOGRAPHY-MASS SPECTROMETER (LC-MS) ANALYSIS

(75) Inventors: Jean-Pierre Chervet, Amsterdam (NL); Remco Swart, Bussum (NL); Johannes Petrus Cornelus Vissers, Huizen (NL)

(73) Assignee: Dionex Corporation, Sunnyvale, CA (US)

( * ) Notice: Subject to any disclaimer, the term of this patent is extended or adjusted under 35 U.S.C. 154(b) by 0 days.

(21) Appl. No.: 09/970,544

(22) Filed: Oct. 3, 2001

(65) Prior Publication Data

US 2002/0072126 A1 Jun. 13, 2002

Related U.S. Application Data

(60) Provisional application No. 60/237,588, filed on Oct. 3, 2000.

(51) Int. Cl.[7] .............................................. G01N 30/02
(52) U.S. Cl. ........................ 436/161; 436/173; 436/178; 422/70; 73/61.56; 73/61.58; 210/656; 210/659; 210/198.2
(58) Field of Search ........................... 422/70; 436/161, 436/173, 178; 73/61.56, 61.58; 210/656, 659, 198.2

(56) References Cited

U.S. PATENT DOCUMENTS

| | | | |
|---|---|---|---|
| 5,240,577 A | * | 8/1993 | Jorgenson et al. .......... 210/656 |
| 6,139,734 A | | 10/2000 | Settlage et al. .......... 210/198.2 |
| 6,402,946 B1 | * | 6/2002 | Spraul et al. ............ 210/198.2 |

FOREIGN PATENT DOCUMENTS

EP    0 495 255    7/1992

OTHER PUBLICATIONS

Aebersold and Goodlett. "Mass Spectrometry in Proteomics," *Chem Rev* 101(2):269–295 (2001).
Davis, M. et al., "A microscale electrospray interface for on–line capillary liquid chromatography/tandem mass spectrometry of complex peptide mixtures," *Anal. Chem* 1995 67(24):4549–4556.
Davis, M. et al., "Variable flow liquid chromatography–tandem mass spectrometry and the comprehensive analysis of complex protein digest mixtures," *J Amer Soc Mass Spectrom* 1997 8(10):1059–1069.
Martin, S. et al., "Subfemtomole MS and MS/MS Peptide Sequence Analysis Using Nano–HPLC Micro–ESI Fourier Transform Ion Cyclotron Resonance Mass Spectrometry," *Anal Chem* 72(18):4266–4274 (2000).

* cited by examiner

*Primary Examiner*—Jan M. Ludlow
(74) *Attorney, Agent, or Firm*—Dorsey & Whitney LLP (57) ABSTRACT

A reconfigurable multi-mode post-column analysis system improves resolution of liquid chromatography detection data by providing a parking or MS/MS detection mode in which flow of column eluent is substantially reduced to provide greater analysis time within a single eluting detection peak. A micro switching valve unit is reconfigurable between normal (MS) mode that passes column eluent directly to an MS unit, and a peak parking (or MS/MS) mode, in which normal mode column flow is interrupted, and the gradient halted, while more slowly flowing the detection peak of interest through the MS unit. A micro syringe pump contributes to the substantially lower MS/MS flow rate. A MS control unit controls micro switching valve valves to reconfigure between MS and MS/MS modes. After a detection peak, MS mode is reestablished, and the system primary pump returns to normal mode flow rate and gradient conditions. Mode changes can be carried out for each chromatogram detection peak.

21 Claims, 7 Drawing Sheets

METHOD AND SYSTEM FOR PEAK PARKING IN LIQUID CHROMATOGRAPHY-MASS SPECTROMETER (LC-MS) ANALYSIS

RELATION TO PREVIOUSLY FILED APPLICATION

This application claims priority from U.S. provisional application Ser. No. 60/237,588 filed on Oct. 3, 2000 and entitled "Device for Controlled Flow Rate Variation and Elution Profile Broadening in Capillary- and Nano Liquid Chromatography".

FIELD OF THE INVENTION

The present invention relates generally to liquid chromatography-mass spectrometer (LC-MS) analyses, and more particularly to so-called peak parking procedures to increases sensitivity and/or collect more MS/MS data from a nano-LC/MS system.

BACKGROUND OF THE INVENTION

Figure 1A:
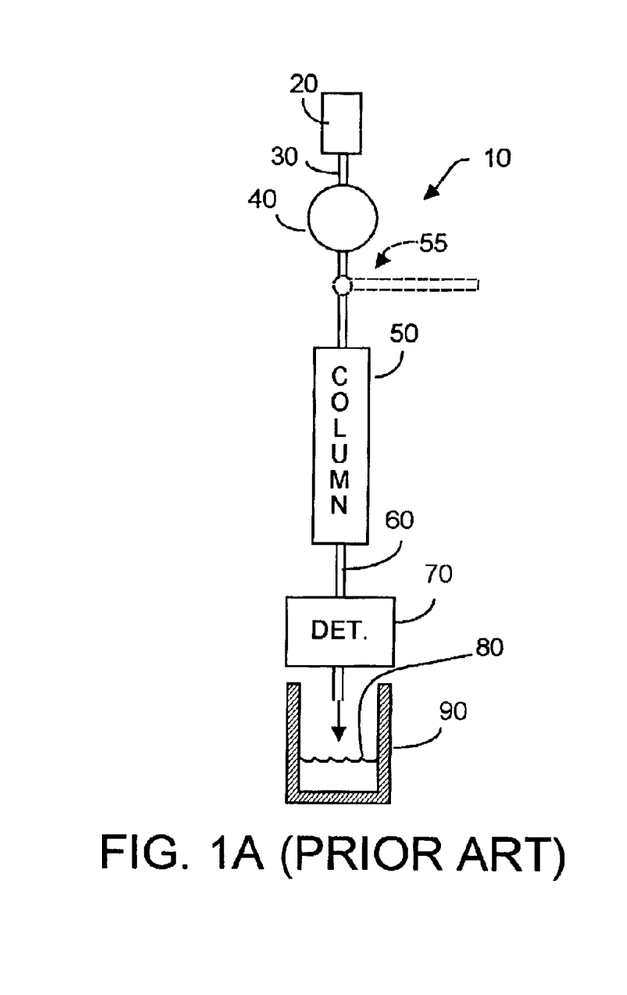
FIG. 1A depicts a conventional liquid chromatography (LC) analysis system, according to the prior art.

Liquid chromatography (LC) is an analytical technique in which a column or tube is packed with a stationary phase material that typically is a finely divided solid or gel. FIG. 1A depicts an LC system 10 in which a source of mobile phase liquid 20 typically contains species to be examined with system 10. The liquid containing species is passed via tubing or the like 30 to a primary pump 40 for input to a column 50 that contains a finely divided solid or gel. Regions within column 50 not occupied by the packing becomes filled with the mobile phase liquid that typically is continuously pumped through the column. A porous plug or filter (not shown) at the lower end of the column in FIG. 1A supports the packing. Those skilled in the art will recognize that in some applications, a pre-column flow splitting configuration is used, indicated in phantom as element 55.

Figure 1B:
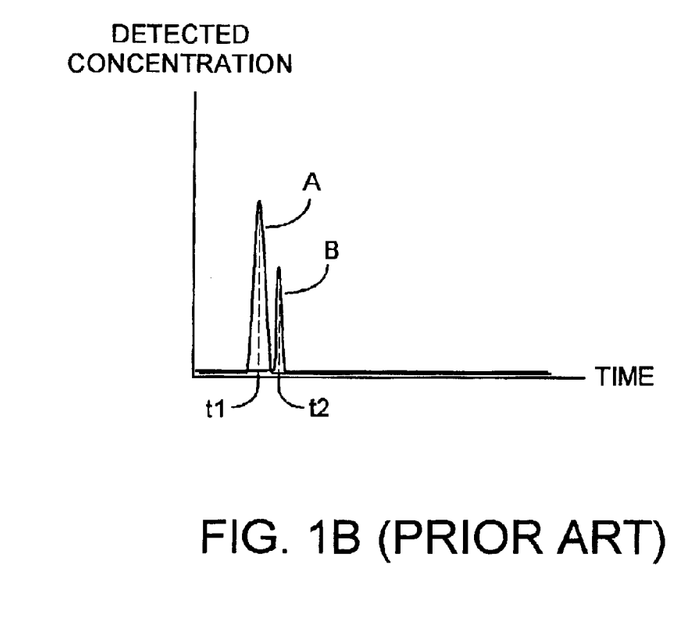
FIG. 1B depicts concentration data for various species, detected in a system such as shown in FIG. 1A, according to the prior art.

Eluent fluid exiting the column through the porous plug passes through tubing 60 (or the like) and is input or otherwise subjected to a detector 70, which seeks to detect species present in the liquid pumped through the column. As shown in FIG. 1B, concentration of different species (e.g., species A, species B) within the eluent fluid typically will peak at different times, as some species can pass through the column and through the plug more rapidly than other species. Thus in FIG. 1B, detector 70 notes a peak in concentration for species A at time t1, and notes a peak (here a smaller amplitude peak) in concentration for species B at time t2. The earlier peak for species A in FIG. 1B could result from many factors, including a relatively rapid mobility for species A, a smaller molecular size, etc. Typically the liquid and species 80 that has been analyzed with detector 70 is collected in a container 80 and is discarded.

One shortcoming with many LC systems such as system 10 is that it can be difficult for detector 70 to adequately sense when the various species within liquid 20 pass through the system. While FIG. 1B depicts two rather definitive concentration peaks, in practice the various peaks may be difficult to discern. The various peaks may exhibit very close concentration peaks and/or occur very close in time.

In many LC analysis systems, liquid 20 may be a biological sample that is difficult to obtain and that is analyzed with a so-called nano-sized capillary column. Understandably it is desired that such valuable liquid samples not be discarded until all possible information as to species within can be obtained. However conventional LC systems such as shown in FIG. 1A are somewhat limited in the analysis that can be carried out with conventional detectors. Where the fluid under analysis includes cellular extracts and/or biological fluids, numerous amounts of proteins will be present. In applications such as proteomics, it is desired to identify these proteins, for example to help elucidate complex medical and biological problems. Identification of proteins that are lacking or over-expressed in abnormal cells is of particular interest.

A general strategy for the identification of proteins is to perform a digestion with an enzyme, e.g. trypsin, and then measure the peptide masses using matrix assisted laser desorption ionization mass spectrometry (MALDI-MS). In applications where this method does not allow protein identification, the peptides must be sequenced using fragmentation mass spectrometry. The measured amino acid sequence of a peptide is then compared with theoretical sequences from protein databases. Mass spectrometric (MS) detection requires that compounds be ionized and in gas phase. Electrospray ionization (ESI) is a commonly applied technique when dealing with biomolecules such as peptides and proteins. In ESI, a potential is applied to the outlet of a conducting needle to spray sample and solvent within. The solvent droplets disintegrate and the solvent evaporates. In so-called nanospray, the sample is sprayed from a needle with a tip diameter less than about 5 $\mu$m, using a sample flow rate between 5 nl/min. and 50 nl/min. Nanospray MS is used for the analysis of low fmol amounts of peptides in small sample volumes. However, most samples are too complex for direct nanospray MS analysis and require some physical separation.

High performance liquid chromatography (HPLC) can be used for high resolution peptide separation, and may readily be used on-line with ESI-MS analysis. In addition, HPLC on-line connected to MS offers the possibility for pre-concentration of dilute samples, desalting and removal of detergents. Available sample amounts in proteomic research are often limited and relatively precious. Therefore it can be very important to carry out analysis using a minimal amount of biological molecules.

In many applications, and especially where relatively small volumes of sample are under analysis, improving detection sensitivity can become especially important. Improvement of detection sensitivity using concentration sensitive detectors such as UV/Vis absorbance and ESI mass spectrometers can be achieved by employing HPLC columns with smaller internal diameters (I.D.). For example, increased sensitivity during peptide analysis can result from using nano- and capillary LC with column I.D.s of 50 $\mu$m and 300 $\mu$m, respectively. Flow rate of the mobile phase through such columns is from several nl/min, to several $\mu$l/min, and the mobile phase can be sprayed directly without splitting.

For maximum LC separation resolution, peak widths should be minimal, but narrow peaks limit the acquisition time for mass spectral data. Preferably, an analytical system should enable separation of all compounds within an HPLC system (narrow peaks and high peak capacity), while enabling essentially unlimited time to acquire mass spectrometric data for each separated compound. For example, peak width at half height of compounds eluting from capillary- or nano-LC columns is generally in the range of 5 seconds to 30 seconds. During this period, the peptide must be sequenced, which requires multiple stages of MS detection. The peptide must be identified, isolated, and dissociated to produce fragment ions. Sequencing of the peptides is performed by comparing measured and calculated fragment spectra. These scan cycles take approximately a few seconds, which allows the experiment to perform only limited cycles during the elution of a chromatographic peak.

Reducing the flow rate during an HPLC experiment can increase the elution time window. Preferably, a reduction of the mobile phase flow rate should instantaneously be effective when the mass spectrometer detects a compound, for example as shown by Lee et al., "A Microscale Electrospray Interface for On-Line, Capillary Liquid Chromatography Tandem Mass Spectrometry of Complex Peptide Mixtures", Anal. Chem. 1995, 67, 4549–4556. Lee disclosed storing a preformed gradient in a loop, and using a programmable syringe pump to slow the mobile phase flow rate. To compensate the delay time before the low flow rate was achieved, the direction of the pump was reversed to try to quickly lower the column head pressure. While this experimental system seemed to work for Lee et al., it is typically not possible to reverse the flow rate with most widely used HPLC pumps, which are reciprocating pumps. Further, flow reversal in a Lee type system that decreases the column inlet pressure can result in severe damage to the column bed and can reduce column lifetime. Further, such flow reversal can cause severe band broadening of the components that are still in the separation column.

U.S. Pat. No. 6,139,734 to Settlage et al. describes a system to perform variable flow rate chromatography using two different lengths of fused silica capillaries that functioned as restrictors. However in practice, one cannot easily control or adjust flow rate through a column, especially if a restrictor becomes partially clogged. Further, Settlage's system splits the injected sample, a procedure that is not acceptable for sample limited applications in proteomics. An additional drawback of a Settlage type system is a loss of separation efficiency due to flow reduction. In practice, a certain time is required to actually reduce the flow rate through Settlage's column due to the relaxation of the column pressure. Unfortunately, during this time a significant part of an eluting peak could already have been detected by the MS, thereby minimizing the advantage of flow reduction on sensitivity.

Thus there is a need for an improved LC analysis system that provides better resolution or granularity of detection information as to species within a liquid sample under examination. Further, such system should provide additional analytical tools to extract as much information as possible from the sample before it is discarded, preferably by broadening elution peaks without loss of chromatographic resolution, while enabling good control of the eluent flow rate. In biotechnology applications, not only such enhanced and further data be provided, but such data should be provided while using relatively small amounts of sample.

The present invention provides such a system and a method for implementing same.

SUMMARY OF THE INVENTION

The present invention provides a reconfigurable multi-mode post-column analysis system that enables improved resolution of liquid chromatography detection data. The invention includes an electrically actuable two-position multi-port micro switching valve unit that is rapidly and rotatably reconfigurable. In normal (or MS) mode, the micro switching value unit is configured to provide fluid communication for column eluent that has passed through a flow cell to directly enter a mass spectrometer (MS) unit. However in a peak parking mode (during which the MS unit preferably operates in an MS/MS mode), the micro switching valve unit is configured to interrupt normal mode column flow and halt the gradient, while flowing the detection peak of interest at a substantially reduced flow rate through the MS unit. The underlying column system with which the present invention may be practiced includes a pre-column primary pump that establishes a normal mode flow rate, but which rate is reduced when the present invention is in peak parking mode.

The invention further includes a micro syringe pump coupled to one of the micro switching valve ports that in peak parking mode provides fluid communication to the MS unit. The micro syringe pump generates a flow rate that is substantially lower than the normal MS flow rate, and delivers, via the micro switching valve, liquid that transports the column contents between the micro switching valve and the MS into the MS. As such, the micro syringe pump functions as a secondary pump and/provides a mechanism to adjust MS/MS flow rate independently from the pre-column pump-established normal mode flow rate. A control unit coupled to the MS commands operation of the ports in the micro switching valve unit commanding reconfiguration from MS mode to MS/MS or parking mode, to MS mode, etc., and further can command the pre-column pump to reduce flow rate in MS/MS mode. The micro syringe pump transports separated compounds into the MS, and the reduced MS/MS mode flow rate increases data acquisition time of MS detection by the ratio between normal mode flow rate through the chromatographic column, and the substantially slower flow rate delivered by the micro syringe pump.

At the end of a detection peak, the control unit commands the micro switching valve unit to return to MS mode configuration, and the primary pump to return to normal delivery flow rate and gradient conditions. The mode change procedure can be carried out for each detection peak in the resultant chromatogram. Flow rate in MS/MS mode may be 20% or less compared to normal MS flow rate, which reduction can extend analysis time over detection peaks of interest. As a result, measurement time for a desired precursor ion selection and for MS/MS analysis within the context of a single eluting peak may be advantageously extended.

Other features and advantages of the invention will appear from the following description in which the preferred embodiments have been set forth in detail, in conjunction with the accompanying drawings.

DETAILED DESCRIPTION OF THE PREFERRED EMBODIMENTS

As will now be described with reference to FIGS. 2A–2C, the present invention permits halting flow rate during capillary- and nano liquid chromatography, and simultaneously transporting detected elution peaks at a substantially lower than normal flow rate using a micro syringe pump as secondary pump. The reduced flow rate increases peak elution time and consequently increases data acquisition time. The invention exhibits a relatively small dead volume and enables chromatographic resolution to be preserved, even under nano LC conditions.

Figure 2A:
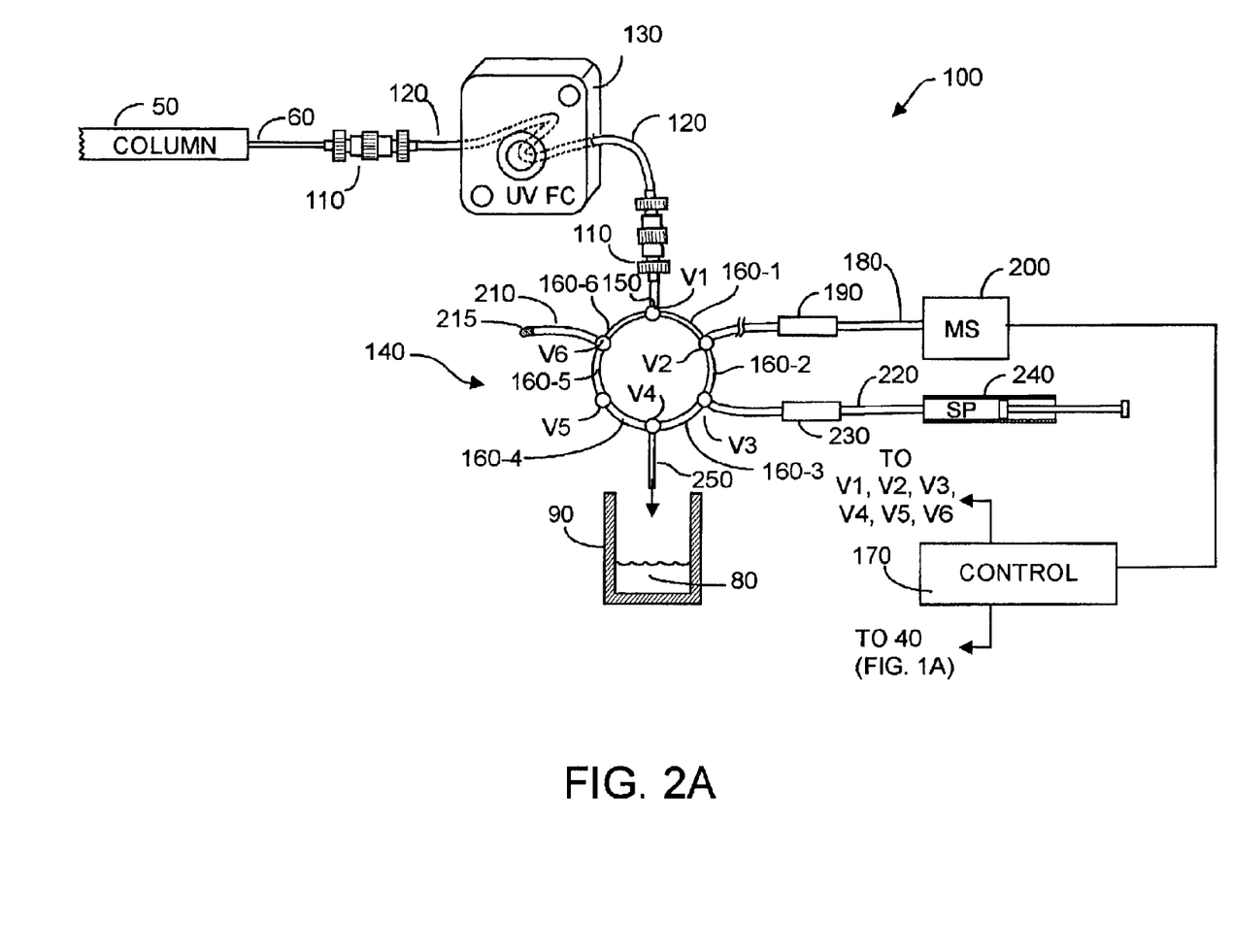
FIG. 2A depicts a peak parking system in which a micro switching valve unit can be controlled to vary eluent flow rate through regions of the micro switching valve such that elution time of column-separated compounds can be extended to enhance detection, according to the present invention.

Turning now to FIG. 2A, a multi-mode system 100 is shown, according to an embodiment of the present invention. System 100 may be employed downstream from a column 50, for example an HPLC column such as used and described with respect to FIG. 1A, to control elution time of compounds that have been separated using a chromatographic column, e.g., column 50. A micro switching valve 140 is used to reconfigure system 100 between a normal or MS mode and a peak parking or MS/MS mode. The micro switching valve includes a two-way rotor mechanism, preferably six ports, and six fluid carrying segments, and is rotatably electro-mechanically reconfigurable, typically within perhaps 100 ms. In the normal or MS mode, eluent flows into a mass spectrometer (MS) unit 200 at a normal flow rate, perhaps 50 nl/minute to 300 nl/minute and typical peak elution times are about 5 seconds to 30 seconds. By contrast, in the peak parking or MS/MS mode, flow rate into MS unit 200 is substantially reduced. By "substantially reduced" it is meant that flow rate is decreased from normal by a factor of perhaps four to ten, or typically 5 nl to about 50 nl/minute. In one embodiment, peak parking (or MS/MS) flow rate is only about 25 nl/minute, and peak elution times are extended to about one to three minutes. As will be described, peak parking or IMS/MS mode advantageously facilitates enhanced resolution of chromatographic peaks eluting from the column 50.

In FIG. 2A, eluent output from column 50 is typically coupled via tubing 60, high pressure connector 110, tubing 120 through a preferably UV flow cell (UV FC) 130. High pressure connectors 110 are used the couple the outlet of column 50 to the inlet of UV FC 130, and to couple the outlet of UV FC 130 to the input of micro switching valve unit 140. Suitable high pressure connectors are the Microtight™ connector available from Upchurch Scientific, Oak Harbor, Wash., US. Other interconnections need not withstand high pressure, and standard Teflon™-type sleeves may be used, e.g., at 190, 230, which interconnections can withstand pressures up to about 10 bar (150 psi). Output from the typically fused silica outlet port of UV FC 130 is coupled via tubing 120 and a second high pressure connector 110 to the input port 150 of a micro switching valve 160. Preferably tubing 120 includes a sleeve of polyetheretherketone (PEEK) material, a nut and a ferrule, although other tubing material may be used. Alternatively, fluid coupling from flow cell 130 may be achieved directly, e.g., using a microfitting. Micro switching valve 160 preferably comprises six ports V1, V2, V3, V4, V5, V6 coupled between six fluid carrying segments or regions 160-1, 160-2, 1603, 160-4, 160-5, and 160-6, as shown. Under command from a control unit 170 that is coupled to receive a control signal from mass spectrometer unit 200, a port can be caused to direct fluid flow to a segment coupled to the port, or to block fluid flow to that segment. (In practice control unit 170 may be an integrated circuit board contained within MS unit 200.) For example, port V1 can enable fluid communication between micro switching valve input 150, segment 160-1, and port V2, or port V1 might instead be set to provide fluid communication between input 150, segment 160-6, and port V6.

As further shown in FIG. 2A, port V2 is coupled via tubing 180 and any necessary interface 190 to a source of ions for MS unit 200. In practice tubing 180 may be a portion of fused silica capillary with an I.D. between 15 $\mu$m and 25 $\mu$m (140), although other materials having other dimensions may also be used. Relative to the micro switching valve input 150, a second port V6 is coupled to a portion of tubing 210 that is blocked with a plug or the like 215. Another port V3 is coupled via a portion of capillary tubing 220 and any necessary interface 230 to the outlet of a syringe pump unit 240 (SP). Another port V4 is coupled to an outlet portion of tubing 240 whose distal end permits eluent in tubing 250 to be collected as fluid 80 in a receptacle 90.

Preferably syringe pump unit 240 includes a 25 $\mu$l or 50 $\mu$l gas-tight syringe such that SP 240 can be set to any substantially constant flow rate between about 5 nl/minute and 50 nl/minute. As will described, the ability of SP 240 to introduce a reduced flow rate in MS/MS mode permits broadening of chromatographic peaks. In the embodiment of FIG. 2A, the reduced flow is coupled from SP 240 to micro switching valve 140 via a piece of fused silica capillary 220 that preferably has an I.D. between about 25 $\mu$m and 50 $\mu$m.

Figure 2B:
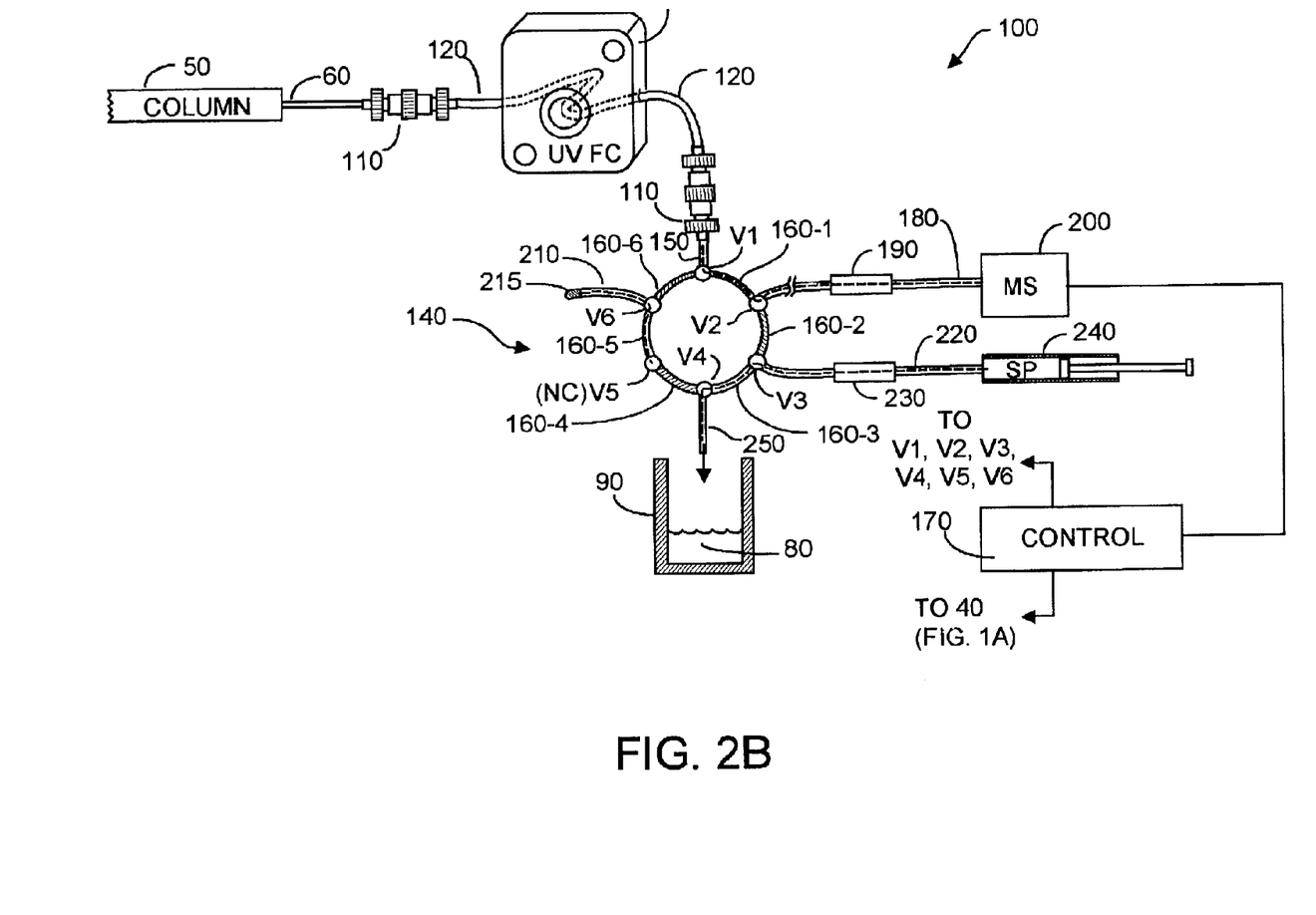
FIG. 2B depicts the system of FIG. 2A in which the micro switching valve unit is configured to produce a normal MS elution mode, according to the present invention.
Figure 2C:
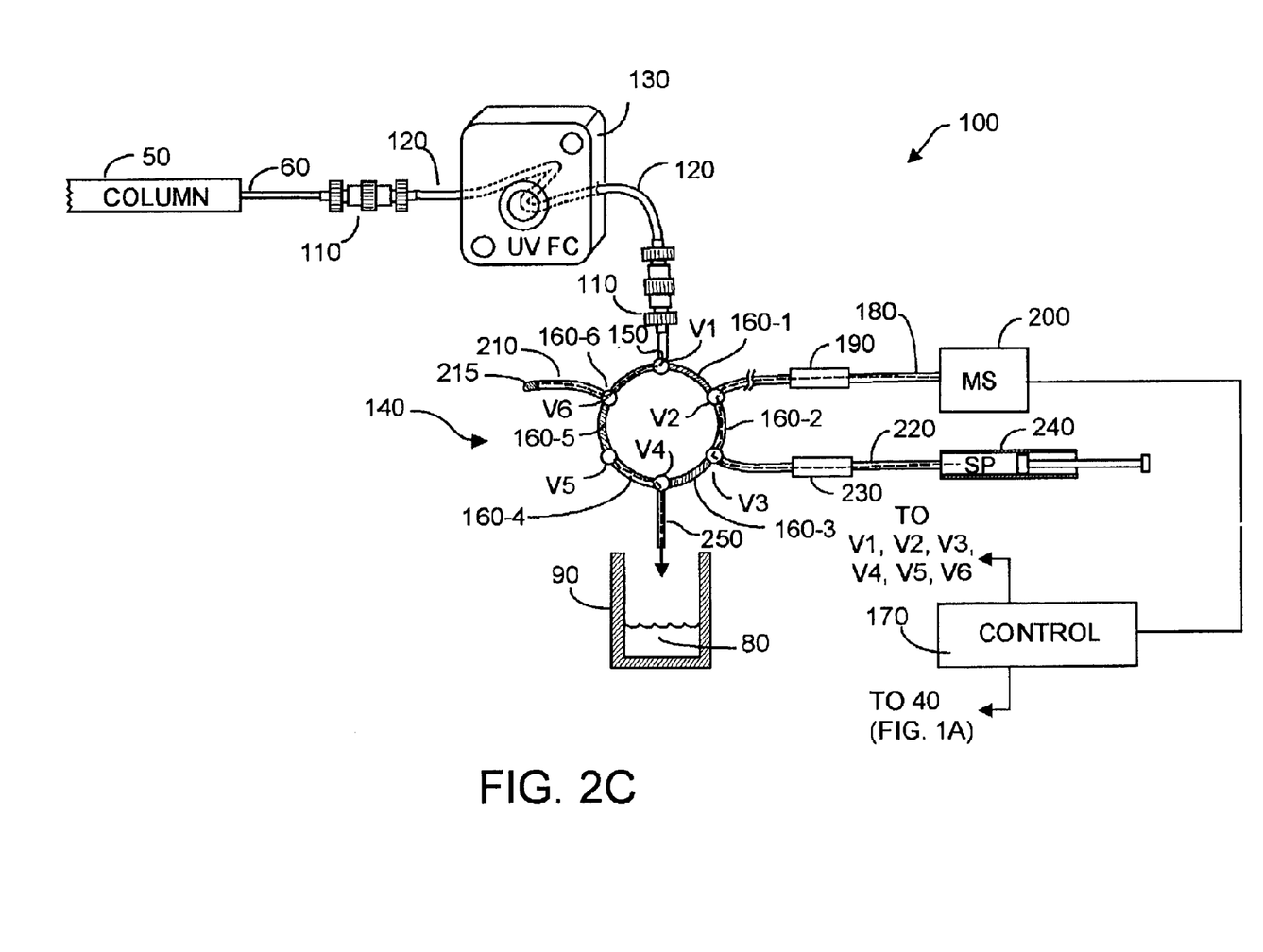
FIG. 2C depicts the system of FIG. 2A in which the micro switching valve unit is configured to produce a peak parking or MS/MS elution mode whose reduced flow rate enhances detection, according to the present invention.

Comparing FIG. 2B and FIG. 2C, it will be seen that control unit 170 (or other control mechanism) can configure the settings of ports V1–V6 to direct fluid flow in a desired configuration or orientation through micro switching valve 140, and through MS unit 200. Preferably micro switching valve unit 140 and upstream primary pump 40 (see FIG. 1A) are triggered by common electrical contact closures, e.g., from controller unit 170. MS units 200 and/or controller units 170 that can provide data dependent contact closures are readily available. Typically software controls MS unit 200 and/or controller unit 170 such that a triggering contact closure is generated only when MS unit 200 detects a signal exceeding a preset threshold value. Thus, MS unit 200 and/or controller unit 170 can automatically toggle system 100 from MS mode into peak parking MS/MS mode, or vice versa, dynamically as a function of the signal detected by MS 200. Note that in MS/MS mode, primary pump 40 preferably is commanded to slow by controller unit 170, such that syringe pump 240 can more readily achieve a very fine and relatively slow flow rate.

In FIG. 2B, control unit 170 commands positions of ports V1–V6 such that system 100 is configured to perform a normal MS mode analysis, an analysis characterized in part by a relatively rapid flow rate. In normal mode, the primary pre-column pump 40 (see FIG. 1A) establishes a relatively high flow rate, perhaps 200 nl/minute. Within micro switching valve 140, cross-hatched segments, e.g., 160-2, 160-4, 160-6 denote segments in which no fluid flow occurs, by virtue of the settings of the ports adjacent these segments. In this normal MS mode, port V1 enables fluid communication such that eluent fluid from column 50 and from UV FC 130 enters input 150, passes via micro switching valve segment 160-1 through tubing 180 to MS unit 200. The phantom lines in FIG. 2B depict this fluid flow path of interest. Note that in the normal mode shown in FIG. 2B, liquid no longer of interest passes via segment 160-3, port V4, tubing 250 and appears as waste 80 in receptacle 90.

Compare now the peak parked or MS/MS mode shown in FIG. 2C. In the configuration of FIG. 2C, control unit 170 causes port Vi to now be in fluid communication with segment 160-6 and port V6, and segment 210, whose distal end is blocked with plug 215. Port V2 is now in fluid communication with segment 160-2, tubing 180 and MS 200, and with port V3, segment 220 and SP 230. Finally, port V5 is in communication with segment 160-4, which is in fluid communication with port V4 and with tubing 250. In addition to controlling micro switching valve 140, MS unit 200 and/or control unit 170 will also command the pre-column pump 40 to reduce its flow rate while system 100 is in peak parked or MS/MS mode.

Column flow rate is halted by micro switching valve unit 140 as soon as a compound of interest elutes into the source of MS unit 200. More specifically, an electrical signal or closure from MS 200 or control unit 170 causes micro switching valve unit 140 to rotate into the new position, here the peak parking position, in which MS unit 200 preferably operates in an MS/MS mode. At the same time, the gradient is paused, and microsyringe pump 240 acts through capillary tubing 220, port V3, segment 160-2, and port V2, tubing 180 to introduce peaks into the MS 200 ionization source. It will be appreciated that microsyringe 240 functions as a secondary pump to establish peak parking mode flow rate substantially independently of flow rate established by pre-column pump 40.

Typically microsyringe 240 can cause the introductory flow rate to be reduced by ,a factor of ten, although other flow rate changes may be used. But advantageously, the improvement in analyte concentration and increased ionization efficiency associated with nanoscale LC are retained. The present invention thus enables selection of a chromatographic peak, and broadening of the peak for increased detection by MS/MS, with minimal loss in chromatographic performance.

System 100 may be used to perform capillary- or nano LC MS of peptides or other biological compounds. By appropriate control switching of micro switching valve 140, mobile phase flow through column 50 is stopped instantaneously. At the same time the gradient formation of the HPLC system is halted, and the flow rate of the gradient or primary pump 40 (see FIG. 1A) is reduced, e.g., under control of control unit 170, to about 50% to about 80% of the initial value. This reduction in flow rate in combination with a pre-column split, e.g., 55 in FIG. 1A, is sufficient to maintain a substantially constant column pressure. The separated compound is transferred into MS unit 200 at the flow rate of syringe pump 240, which acts as a secondary pump. Upon receipt of the next contact closure or pulse from MS 200 and/or controller 170, electrically caused mechanical rotation results in the ports comprising micro switching valve 140 reconfiguring back into normal mode, and a normal flow rate through the column is re-established and the gradient program continues. In normal mode, control unit 170 commands primary pre-column pump 40, see FIG. 1A, to resume normal flow rate operation. With micro switching valve unit 140 rotated into the normal mode configuration, primary pump 40 is caused by controller 170 to return to its original delivery regime and gradient conditions. As noted, such procedure may be carried out in automated fashion for each peak in the chromatogram.

Referring to FIGS. 2A–2C, nano column 50 is preferably coupled to a UV/Vis flow cell 130 using high pressure connector 110. The output side of flow cell 130 was connected to micro switching valve 140, a Valco Cheminert micro switching valve with 0.15 mm port diameter. This unit is catalog number C2-0006D with a (catalog number) C2-OOR6 rotor, mounted on an electrical micro drive. An alternative source for micro switching valve 140 is the Upchurch V-435 6 port micro switching valve, available from Upchurch Scientific, Oak Harbor, Wash., US. Micro syringe pump unit 240 preferably includes a Hamilton gas tight 25 $\mu$l type 1702 syringe, mounted on a Harvard Apparatus Model 11 VPF syringe pump. Micro syringe pump unit 240 delivered a peak parking flow rate of 25 nl/min, as noted above. The above-specified components are exemplary, and other components may be used.

In standard mode micro switching valve 140 was caused to direct the mobile phase through port V1, segment 160-1, tubing 180 to MS unit 200. In peak parking mode, control unit 170 causes the various ports within micro switching valve 140 to switch, and the mobile phase was stopped by plug 215 at the end of tubing 210. Electrospray ionization (ESI) mass spectrometry was conducted with a Q-TOF of hybrid quadrupole/time-of-flight mass spectrometer in the positive ion mode. This MS unit was obtained from Micromass, Altrincham, Ches., UK, although other units could instead be used. Sequencing of the peptides, e.g., tandem mass spectrometry (MS/MS), was carried out in an automated fashion using system 100.

A demonstration of peak parking on chromatographic performance was conducting using two UV/Vis detectors. A first detector, e.g., IV FC 130, monitored mobile phase directly after the nano LC column, and a second detector, e.g., MS 200, was used to measure UV absorbance after peak parking. In actual applications, the second UV/Vis detector resembles a mass spectrometer.

Figure 3A:
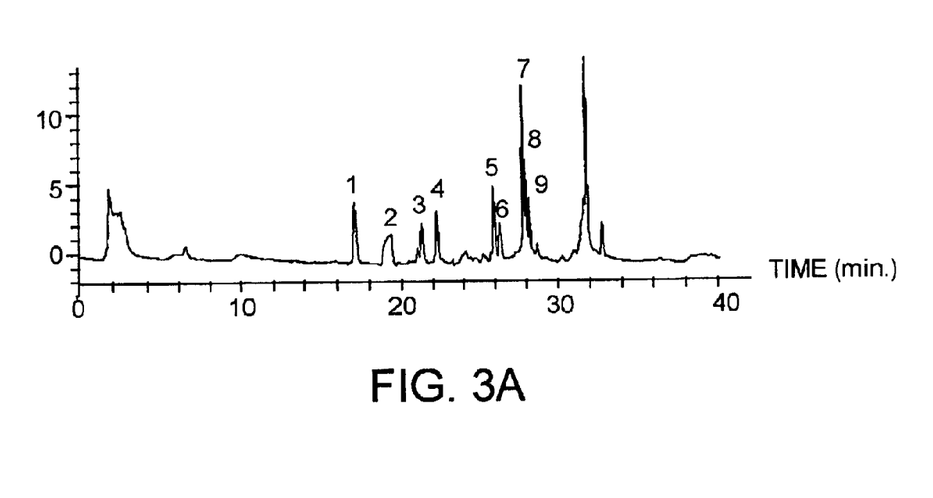
FIG. 3A depicts a normal mode UV chromatogram of a tryptic digest of cytochrome C, according to the prior art.
Figure 3B:
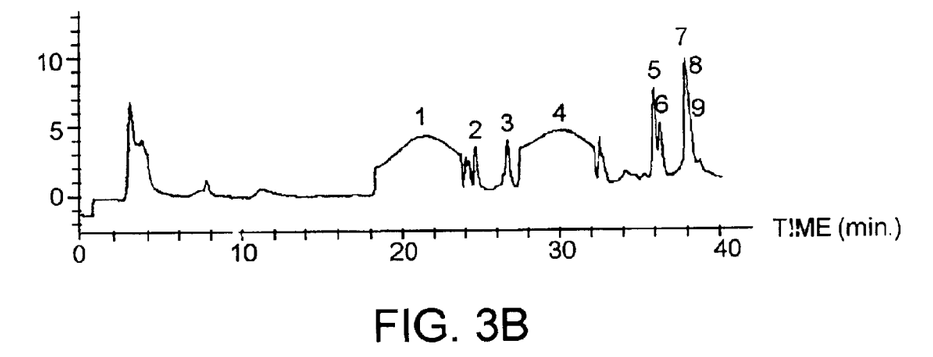
FIG. 3B depicts a park peaking mode UV chromatogram of a tryptic digest of cytochrome C with flow rate reduced for peaks 1 and 4, according to the present invention.

FIG. 3A depicts a UV chromatogram taken from UV FC 130 for a nano LC separation of a tryptic digest of cytochrome C under normal flow rate conditions (e.g., relatively rapid flow rate). By contrast, FIG. 3B depicts detection results from MS unit 200 when system 100 is operated in the peak parking mode, and shows detection of two compounds, depicted as peak 1 and peak 4, for which peaks flow rate was reduced at least in part by SP 240. Referring still to FIG. 3B, when the compound entered the flow cell portion of MS unit 200, control unit 170 caused micro switching valve 140 to switch from MS normal mode into peak parking MS/MS mode, with resultant reduced flow rate. It is apparent from FIG. 3B that elution of peaks 1 and 4 is considerably broadened by the lower flow rate (here 50 nl/minute) resulting from the action of micro syringe pump 230. When the compound passed through MS 200, a second control pulse from control unit 170 caused the various ports in micro switching valve unit 140 to return to the original normal mode, and flow rate was reset to 0.2 $\mu$l/minute. In the mean time, remnant peaks had been 'parked' and could be detected after the peak of interest had finished.

Note that any band broadening influence of micro switching valve unit 140 disposed between column 50 and MS detector 200 is acceptable. Indeed a comparison between the normally eluted peaks in the chromatogram of FIG. 3A and the expanded eluted peaks in the chromatogram of FIG. 3B reveals that peak widths are only slightly larger, which implies that chromatographic resolution is maintained within the entire set-up.

Figure 4A:
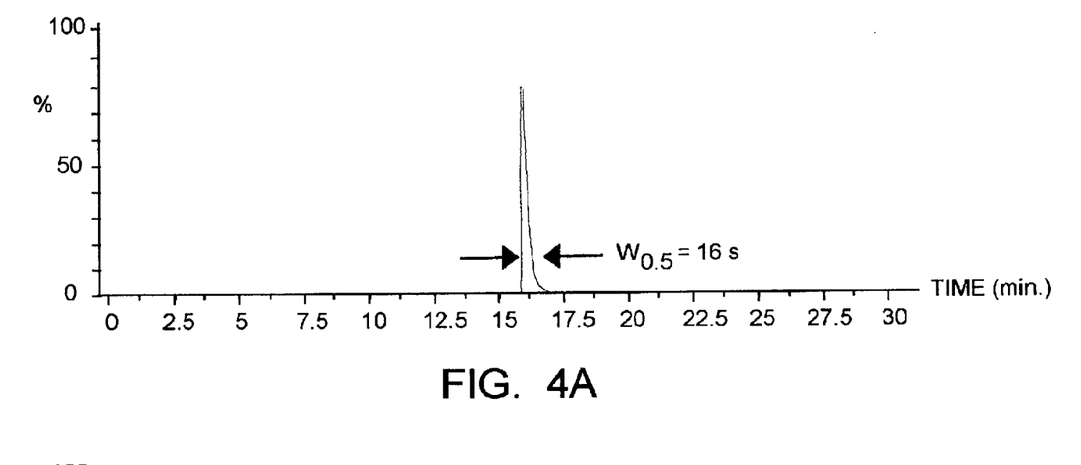
FIG. 4A depicts an ion chromatogram for neurotensin, obtained in normal mode, according to the prior art.
Figure 4B:
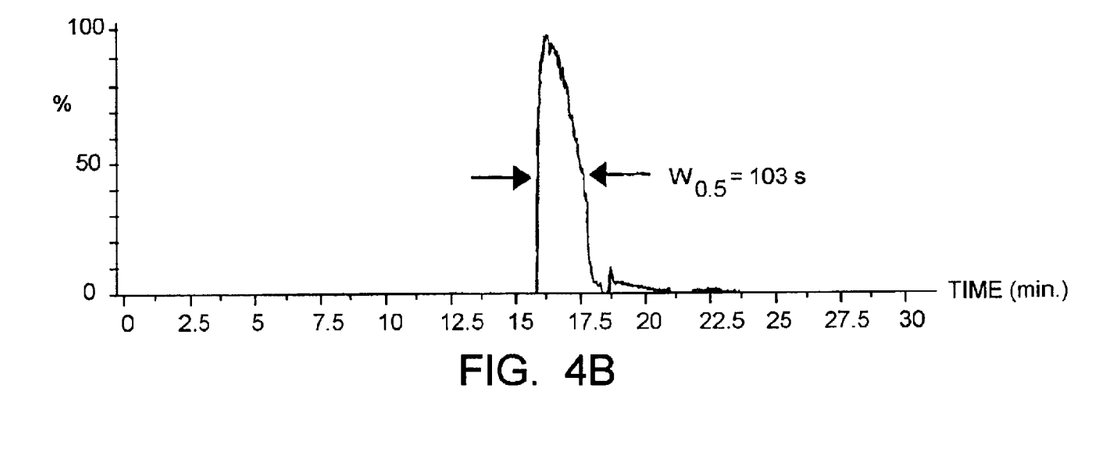
FIG. 4B depicts an ion chromatogram for neurotensin showing enhanced resolution resulting from reduced flow rate conditions in LC/LC mode, according to the present invention.

The results of LC-MS experiments demonstrating the increased sensitivity of MS; detection using peak parking is shown in FIGS. 4A and 4B for the peptide neurotensin. FIG. 4A shows the selected ion trace of neurotensin under normal mode LC conditions using a flow rate of 200 nl/minute, and shows a peak width at half-height of 16 seconds. FIG. 4B shows the same trace in MS/MS mode, where half-height peak width is now 103 seconds, at a reduced flow rate of only 25 nl/minute. Note that a greater than six-fold increase in potential precursor time and MS/MS acquisition time was obtained. Data for FIGS. 4A and 4B were gathered with system 100 in a nano-LC experiment. The analysis was performed on an Ultimate LC system, equipped with a NAN75 calibrator and a nano-LC column that measured 75 $\mu$m I.D.×15 cm length, packed with PepMap™ C18, 3 $\mu$m stationary phase.

The system and stated components are available from LC Packings, Amsterdam, The Netherlands. The primary pumping device was based on precolumn flow splitting and allowed for highly reproducible micro- and nanoliter flow delivery for isocratic and gradient conditions. (See for example EPO patent no. 0495255 to co-inventor J. P. Chervet herein.) Mobile phase A was water containing 0.05% trifluoroacetic acid (TFA) and mobile phase B, the organic eluent, was 80% acetonitrile/water containing 0.04% TFA.

Peptides were eluted with a gradient from 5% to 40% in about 30 minutes. Flow rate through the LC column was 200 nl/minute. A digest of cytochrome C (1.6 pmol) was injected. Cytochrome c and neurotensin were obtained from Sigma, Inc., St. Louis, Mo., US. Cytochrome C was digested overnight with sequencing grade modified trypsin, in 1 ml of ammonium carbonate (pH 8) at a protein:enzyme ratio of 50:1 at 37° C. Sequencing grade modified trypsin is available from Promega Corp., Madison, Wis., US.

Figure 5A:
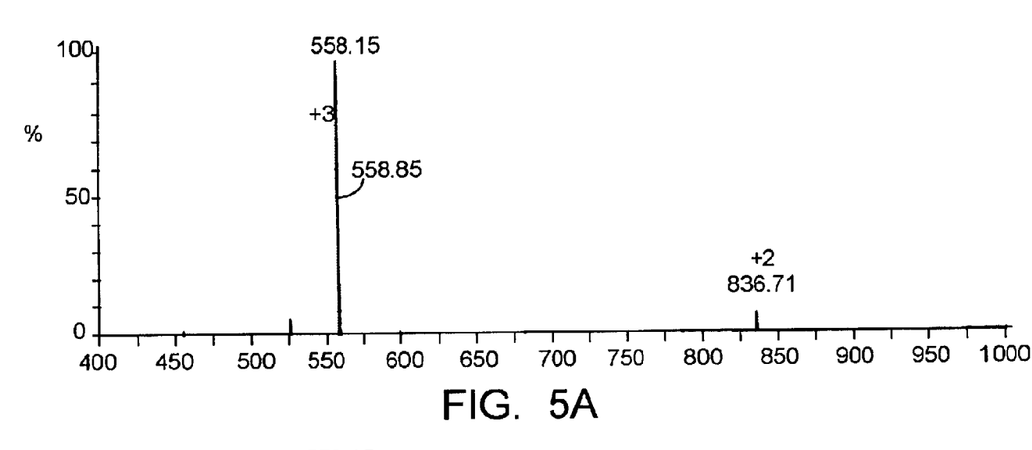
FIG. 5A depicts the summed MS spectra for neuotensin, according to the prior art.
Figure 5B:
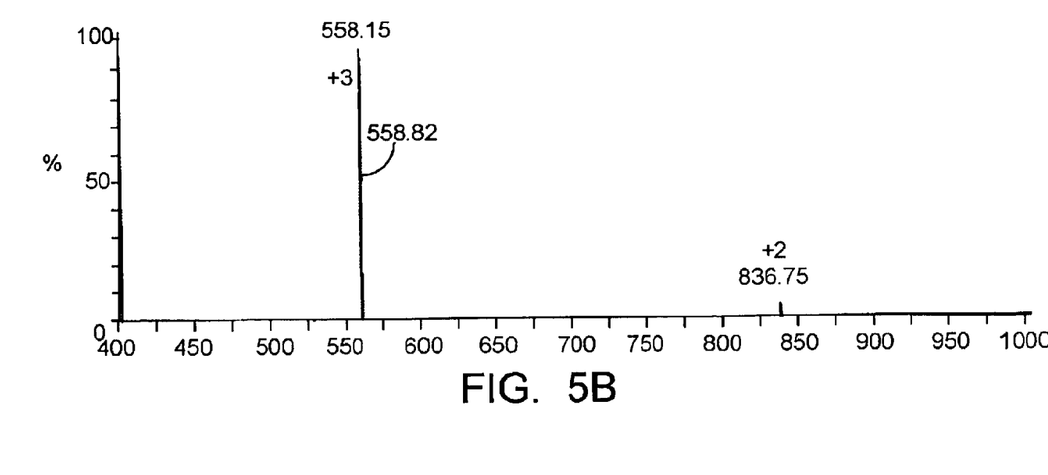
FIG. 5B depicts the summed MS spectra for neuotensin, showing enhanced resolution resulting from reduced flow rate conditions, according to the present invention.

FIGS. 5A and 5B depict result on MS sensitivity of the above procedures. FIG. 5A depicts MS spectra summed across the chromatographic peak for neuotensin, while FIG. 5B depicts the summed MS neuotensin spectra, showing enhanced resolution resulting from reduced flow rate conditions. The ion count for normal mode 200 nl/minute flow rate in FIG. 5A was 3330, while the ion count for reduced 25 nl/minute MS/MS flow rate in FIG. 5B was 25,200, an eight-fold increase.

To recapitulate, in peak parking MS/MS mode, the present invention increases sensitivity and/or collects more MS/MS data per unit time from a Nano- or LC/MS system. Peak parking with a micro switching valve and a micro syringe pump interrupts column flow and pauses the gradient, while moving the peak of interest at a substantially lower flow rate through the MS detector. Electrically reconfiguring the micro switching valve changes system mode, from normal mode to peak parking mode to normal mode to peak parking mode, etc. In peak parking mode, the micro syringe pump generates a reduced flow rate, substantially independently of the pre-column primary pump flow rate that is present in normal mode, and the micro switching valve ports serve to hold the substances (or "peaks") eluting from the column. The micro syringe transfers a peak of interest at a lower MS/MS mode flow rate into the MS detection unit. MS detection sensitivity is enhances because more scans of a given substance, which is to say more spectra for a given precursor ion are acquired, and/or more MS/MS data for multiple co-eluting substances is acquired.

Modifications and variations may be made to the disclosed embodiments without departing from the subject and spirit of the invention as defined by the following claims.

What is claimed is:

1. A method for increasing elution time of chromatographic peaks associated with a post-column detector of a liquid chromatograph system, the method including the following steps:

pumping an eluent flow to a chromatographic column at a first flow rate;

directing the eluent flow from said chromatographic column through a valve unit to said post-column detector in a first, normal mode;

monitoring eluent flow through said post-column detector for peaks;

switching the valve unit to a second, peak-parking mode when a peak is detected by said post-column detector;

the valve unit blocking eluent outflow from said chromatographic column during said second, peak-parking mode;

providing a secondary fluid flow at a second flow rate through said valve unit to said post-column detector during said second, peak-parking mode, wherein the second flow rate is substantially less than said first flow rate.

2. The method of claim 1, wherein said second flow rate during said second, peak-parking mode is approximately 10% to 50% of said first flow rate during said first, normal mode.

3. The method of claim 1, further including maintaining a substantially constant pressure over said chromatographic column during said second, peak-parking mode.

4. A liquid chromatography setup that includes a chromatographic column through which a mobile phase having at least one component passes as eluent for analysis by a post-column detector, and a post-column analysis system to increase elution time of chromatographic peaks associated with detection by said post-column detector, said post column analysis system including:

a micro-switching valve unit having an input port coupled to said chromatographic column, said micro-switching valve unit being switchable between a first position in which said eluent flows at a first flow rate to said post-column detector, and a second position in which eluent flow through said chromatographic column is halted and a portion of said eluent within a region of said micro-switching valve unit flows to said post-column detector at a second flow rate that is substantially lower than said first flow rate; and a secondary pump system coupled to a portion of said micro-switching valve unit, and operable to contribute to establish said second flow rate when said micro switching valve unit is in said second position;

wherein when said micro switching valve unit is in said second position, said secondary pump system pumps a portion of said eluent retained in a portion of said micro switching valve unit to said post-column detector such that individual detection peaks are input more slowly to said post-column detector;

wherein at least one of said means for selectively passing and halting and said means for substantially reducing contribute to a substantially constant gradient composition during said peak parking mode.

5. A liquid chromatography system comprising a chromatographic column through which an eluent passes for analysis by a post-column detector, a primary pump for pumping the eluent to said chromatographic column at a first flow rate, and an analysis system to increase elution time of chromatographic peaks associated with detection by said post-column detector, said analysis system including:

a secondary pump system for pumping fluid at a second flow rate substantially less than said first flow rate;

a micro-switching valve unit having a primary input port in fluid communication with said chromatographic column, a primary output port in fluid communication with said post-column detector via a detector tubing, a secondary input port in fluid communication with said secondary pump system;

said micro-switching valve unit having a first, normal position that fluidly couples said chromatographic column and said post-column detector, and a second, peak-parking position that fluidly couples said post-column detector with said secondary pump system instead of said chromatographic column, wherein a portion of the eluent in said detector tubing flows into said post-column detector at said second flow rate when said micro-switching valve unit is in said second, peak-parking position such that individual detection peaks are input more slowly to said post-column detector.

6. The liquid chromatography system of claim 5, further including a control unit coupled to said post-column detector and said micro-switching valve, wherein said control unit switches said micro-switching valve unit to said second position when a detection peak is sensed by said post-column detector, and to said first position when a said detection peak ends:

said control unit further coupled to said secondary pump to control flow rate thereof as a function of whether said micro-switching valve unit is in said first position or is in said second position.

7. The liquid chromatography system of claim 6, wherein:

said control unit is coupled to said primary pump and reduces said first flow rate when said micro-switching valve unit is in said second position.

8. The liquid chromatography system of claim 5, wherein:

said secondary pump system includes a syringe pump; and said second flow rate is approximately 10% to 50% of said first flow rate.

9. The liquid chromatography system of claim 5, wherein said liquid chromatography system is selected from a group consisting of (a) a capillary liquid chromatography system, and (b) a nano liquid chromatography system.

10. The liquid chromatography system of claim 5, wherein when said micro-switching valve unit is in said second position, said control unit controls said primary pump to maintain a substantially constant pressure in said chromatographic column.

11. The liquid chromatography system of claim 5, wherein said micro-valve unit has an internal volume less than approximately 5 µl.

12. The liquid chromatography system of claim 5, wherein:

said first flow rate is approximately 50 nl/minute to 400 nl/minute; and said second flow rate is approximately 5 nl/minute to about 50 nl/minute.

13. The liquid chromatography system of claim 5, wherein said post-column detector includes at least one of (a) a mass spectrometer, and (b) a nuclear resonance detector.

14. The liquid chromatography system of claim 5, wherein said liquid chromatography system includes pre-column flow splitting enabling delivery of microflow and nanoflow over said chromatographic column.

15. The liquid chromatography system of claim 5, wherein when said micro-switching valve unit is in said second position, gradient composition is maintained substantially constant.

16. The liquid chromatography system of claim 5, wherein when said micro-switching valve is in said second position, said micro-switching valve unit halts chromatographic process by blocking outflow from said column, and when said micro-switching valve is in said second position, inlet flow rate to said chromatographic column is reduced by approximately 50% to about 80% using a pre-column split.

17. An analysis system for increasing elution time of chromatographic peaks associated with detection by a post-column detector, the analysis system configured for use with a liquid chromatography system having a chromatographic column through which a mobile phase passes as eluent for analysis by the post-column detector, and a primary pump for pumping the eluent through said chromatographic column at a first flow rate, said analysis system comprising:

a secondary pump for pumping fluid at a second flow rate substantially less than the first flow rate of the primary pump;

a valve unit having a primary input port configured for fluid coupling with the chromatographic column, a primary output port for fluid coupling with the post-column detector, and a secondary input port fluidly coupled to said secondary pump, said valve unit having a first, normal mode that fluidly couples said primary input port to said primary output port, and a second, peak-parking mode that fluidly couples said secondary input port to said primary output port; and a control unit operably coupled with said valve unit and configured to switch said valve unit between said first and second modes dependent upon a signal received from the post-column detector, said control unit configured to actuate said secondary pump when said valve unit is in said second, peak parking mode.

18. The analysis system of claim 17, wherein said valve unit includes a micro-switching valve unit having a plurality of two-way valves and a plurality of ports between adjacent ones of said two-way valves.

19. The analysis system of claim 17, wherein said secondary pump includes a micro-syringe pump and said control unit is configured to operatic said micro-syringe pump during said second, peak-parking mode, to provide a flow rate of approximately 10% to 50% of the first flow rate.

20. The analysis system of claim 17, wherein at least one of said valve unit and said control unit are configured to facilitate a substantially constant pressure in said chromatographic column during when said valve unit is in said second, peak-parking mode.

21. The analysis system of claim 17, wherein at least one of said valve unit and said control unit are configured to substantially maintain a constant gradient composition during when said valve unit is in said second, peak-parking mode.

\* \* \* \* \*